(12) United States Patent
Choulika et al.

(10) Patent No.: US 7,960,525 B2
(45) Date of Patent: *Jun. 14, 2011

(54) GENE REPAIR INVOLVING IN VIVO EXCISION OF TARGETING DNA

(75) Inventors: André Choulika, Paris (FR); Richard C. Mulligan, Lincoln, MA (US)

(73) Assignees: The Institute Pasteur, Paris (FR); The Children's Medical Center Corporation, Boston, MA (US)

( * ) Notice: Subject to any disclaimer, the term of this patent is extended or adjusted under 35 U.S.C. 154(b) by 637 days.

This patent is subject to a terminal disclaimer.

(21) Appl. No.: 11/904,034

(22) Filed: Sep. 25, 2007

(65) Prior Publication Data

US 2009/0060896 A1 Mar. 5, 2009

Related U.S. Application Data

(63) Continuation of application No. 10/336,069, filed on Jan. 2, 2003, now Pat. No. 7,285,538, which is a continuation of application No. 09/922,495, filed on Aug. 3, 2001, now abandoned, which is a continuation of application No. PCT/US00/02949, filed on Feb. 3, 2000.

(60) Provisional application No. 60/118,472, filed on Feb. 3, 1999.

(51) Int. Cl.
*A61K 48/00* (2006.01)
*C07H 21/02* (2006.01)
*C12N 15/00* (2006.01)

(52) U.S. Cl. .................. 536/23.1; 514/44 R; 435/320.1

(58) Field of Classification Search ......................... None
See application file for complete search history.

(56) References Cited

U.S. PATENT DOCUMENTS

| 5,436,150 | A | 7/1995 | Chandrasegaran |
| 5,674,499 | A | 10/1997 | Willemse et al. |
| 5,792,632 | A | 8/1998 | Dujon et al. |
| 5,830,729 | A | 11/1998 | Jaisser et al. |
| 5,962,327 | A | 10/1999 | Dujon et al. |
| 6,238,924 | B1 | 5/2001 | Dujon et al. |
| 7,098,031 | B2 | 8/2006 | Choulika et al. |
| 7,285,538 | B2 | 10/2007 | Choulika et al. |
| 7,629,326 | B2 | 12/2009 | Choulika et al. |
| 2002/0107214 | A1 | 8/2002 | Choulika et al. |
| 2002/0110898 | A1 | 8/2002 | Choulika et al. |
| 2004/0019002 | A1 | 1/2004 | Choulika et al. |

FOREIGN PATENT DOCUMENTS

| WO | WO 96/14408 | 5/1996 |
| WO | WO 00/46386 | 8/2000 |

OTHER PUBLICATIONS

Notification of Transmittal of the International Search Report (ISR) or the Declaration, with ISR, PCT/US2000/02949, mailed Jul. 6, 2000.

Invitation to Restrict or to Pay Additional Fees, PCT/US2000/02949, mailed Nov. 16, 2000.

Written Opinion, PCT/US2000/02949, mailed Jan. 26, 2001.

Notification of Transmittal of the International Preliminary Examination Report (IPER), with IPER, PCT/US2000/02949, mailed May 23, 2001.

Choulika, A. et al., "The Yeast I-SCE I Meganuclease Induces Site-Directed Chromosomal Recombination in Mammalian Cells," *C.R. Acad. Sci. III*, 317:1013-1019 (1994).

Cohen-Tannoudji, M., et al., "I-*Sce*I-Induced Gene Replacement at a Natural Locus in Embryonic Stem Cells," *Mol. Cell. Biol.* 18(3):1444-1448 (Mar. 1998).

Choulika, A. et al., "Induction of Homologous Recombination in Mammalian Chromosomes by Using the I-SceI System of Saccharomyces cerevisiae," *Molecular and Cellular Biology*, 15(4):1968-1973 (1995).

Smith, J. et al., "A Detailed Study of the Substrate Specificity of a Chimeric Restriction Enzyme," *Nucleic Acids Res.*, 27(2):674-681 (Jan. 15, 1999).

Nahon, E. and Raveh, D., "Targeting a Truncated Ho-Endonuclease of Yeast to Novel DNA Sites with Foreign Zinc Fingers," *Nucleic Acids Res.*, 26(5):1233-1239 (1998).

Kim, Y.G. et al., "Hybrid Restriction Enzymes: Zinc Finger Fusions to Fok I Cleavage Domain," *Proc. Natl. Acad. Sci. USA*, 93(3):1156-1160 (1996).

Anderson, W.F., "Human Gene Therapy," *Nature*, 392:25-30 (Apr. 30, 1998).

Nishikawa, M. et al., "Nonviral Vectors in the Millennium: Delivery Barriers in Gene Transfer," *Human Gene Therapy*, 12:861-870 (2001).

Rozenberg, Y. et al., "Alternative Gene Delivery," *S.T.P. Pharma Sciences*,11:21-30 (2001).

Balicki, D. et al., "Gene Therapy of Human Disease," *Medicine*, 81:69-86 (2002).

Orkin, S. H. and Motulsky, A.G., "Report and Recommendations of the Panel to Assess the NIH Investment in Research on Gene Therapy", National Institutes of Health, 1-41 (Dec. 7, 1995).

Verma, I. M. et al., "Gene Therapy-Promises, Problems and Prospects," *Nature*, 389:239-242 (1997).

Ross, G. et al., "Gene Therapy in the United States: A Five-Year Status Report," *Human Gene Therapy*, 7:1781-1790 (1996).

Marshall, E., "Gene Therapy's Growing Pains," *Science*, 269:1050-1055 (1995).

"There are Common Motifs in Many Sequence-specific DNA-binding Proteins," In *Molecular Biology of the Cell*, 2nd ed. Alberts, B. et al.(eds). (Garland Publishing, New York), Chap. 9, p. 490 (1989).

Promega "Revolutions in Science," 1993/1994 Catalog, p. 20.

Belfort, M. and Roberts, R.J., "Homing endonucleases: keeping the house in order," *Nucleic Acids Res.* 25(17): 3379-3388 (1997).

(Continued)

*Primary Examiner* — Robert M Kelly
(74) *Attorney, Agent, or Firm* — Hamilton, Brook, Smith & Reynolds, PC

(57) ABSTRACT

Methods of modifying, repairing, attenuating and inactivating a gene or other chromosomal DNA in a cell are disclosed. Also disclosed are methods of treating or prophylaxis of a genetic disease in an individual in need thereof.

9 Claims, 3 Drawing Sheets

OTHER PUBLICATIONS

Grindl, W., et al., "The protein splicing domain of the homing endonuclease PI-*Sce*I is responsible for specific DNA binding," *Nucleic Acids Res.* 26(8): 1857-1862 (Apr. 15, 1998).

Pósfai, G., et al., "Markerless gene replacement in *Escherichia coli* stimulated by a double-strand break in the chromosome," *Nucleic Acids Res.* 27(22): 4409-4415 (Nov. 15, 1999).

Plessis, A., et al., "Site-Specific Recombination Determined by I-*Sce*I, a Mitochondrial Group I Intron-Encoded Endonuclease Expressed in the Yeast Nucleus," *Genetics* 130:451-460 (Mar. 1992).

Rouet, P., et al., "Expression of a Site-Specific Endonuclease Stimulates Homologous Recombination in Mammalian Cells," *Proc. Natl. Acad. Sci. USA* 91:6064-6068 (Jun. 1994).

Gunzburg, W.H. and Salmons, B., "Virus Vector Design in Gene Therapy," Mol. Med. Today 1(9) Abstract (Dec. 1995).

Góorecki, D.C., "Prospects and Problems of Gene Therapy: An Update," *Expert Opin. Emerging Drugs* 6(2):187-198 (2001).

Eck, S.L., and Wilson, J.M., *Goodman & Gilman's The Pharmacological Basis of Therapeutics*, Ninth Ed., Chapter 5, pp. 77-101, McGraw-Hill, New York, 1996.

Deonarain, M.P., "Ligand-Targeted Receptor-Mediated Vectors for Gene Delivery," Exp. Opin. Ther. Patents 8(1):53-69 (Jan. 1998).

Kim, Y-G., and Chandrasegaran, S., "Chimeric Restriction Endonuclease," Proc. Natl. Acad. Sci. USA, 91: 883-887 (1994).

The Children's Medical Center Corporation, et al., PCT/US2000/03014, Invitation to Pay Additional Fees, mailed Jun. 21, 2000, 6 pgs.

The Children's Medical Center Corporation, et al., PCT/US2000/03014, Notification of Transmittal of the International Search Report (ISR) or the Declaration with ISR, mailed Sep. 13, 2000, 11 pgs.

The Children's Medical Center Corporation, et al., PCT/US2000/03014, Written Opinion, mailed Mar. 13, 2001, 6 pgs.

The Children's Medical Center Corporation, et al., PCT/US2000/03014, Notification of Transmittal of the International Preliminary Examination Report (IPER) with IPER, mailed May 25, 2001, 7 pgs.

The Children's Medical Center Corporation, EP 00 908 499.7, Communication, mailed Jan. 19, 2005, 6 pgs.

The Children's Medical Center Corporation, et al., EP 00 908 499.7, Reply, filed Nov. 18, 2005, 7 pgs.

The Children's Medical Center Corporation, et al., EP 00 908 499.7, Summons to attend oral proceedings, mailed Feb. 20, 2007, 8 pgs.

The Children's Medical Center Corporation, et al., EP 00 908 499.7, Response to Summons, filed May 11, 2007, 6 pgs.

The Children's Medical Center Corporation; The Institute Pasteur, Canadian Appl. 2,361,191, Office Action, dated Nov. 13, 2009, 5 pgs.

The Children's Medical Center Corporation, et al, Japan Appl. 2000597445, Office Action, dated Nov. 26, 2009 4 pgs.

The Children's Medical Center Corporation, et al, Japan Appl. 2000597444, Office Action, dated Nov. 25, 2009 4 pgs.

The Children's Medical Center Corporation; The Institute Pasteur, Canadian Appl. 2,360,878, Office Action, dated Aug. 31, 2009, 4 pgs.

The Children's Medical Center Corporation; The Institute Pasteur, Canadian Appl. 2,360,878, Reply, filed Feb. 25, 2010, 18 pgs.

The Children's Medical Center Corporation; The Institute Pasteur, Canadian Appl. 2,360,878, Office Action, dated Jun. 17, 2010, 3 pgs.

| % age of β-gal expressing cells | | No I-SceI site | 2 I-SceI sites | 1 I-SceI sites | linear fragment |
|---|---|---|---|---|---|
| 4 bp deletion repair | I-SceI + | 0 | 0.8-1.2 | 0.09 | 0.001 |
| | I-SceI - | 0 | 0 | 0 | 0.001 |
| 4 bp duplication repair | I-SceI + | 0 | 0-1.6 | 0.2-0.3 | 0.007 |
| | I SceI - | 0 | 0 | 0 | 0.008 |

FIG. 2

| Enzyme | Organism (strain) | Size | Site | Cleavage | Shape of Cleavage | GenBank Accession No. | Commercially Available |
|---|---|---|---|---|---|---|---|
| ENZYMES ENCODED BY INDEPENDENT GENES | | | | | | | |
| Endo.Sce | Saccharomyces cerevisiae (IAM 4274) | 476 | 25 | very frequent | 4'/3'OH | M63839 | |
| HO | Saccharomyces cerevisiae | 586 | 18 | very rare | 4'/3'OH | M14678 | |
| ENZYMES ENCODED BY INTRONS | | | | | | | |
| I-Ceu I | Chlamydomonas eugametos | 218 | 20 | very rare | 4'/3'OH | S15138 | Yes |
| I-Chu I | Chlamydomonas humicola | 218 | 20 | very rare | 4'/3'OH | L06107 | |
| I-Cre I | Chlamydomonas reinhardtii | 163 | 24 | very rare | 4'/3'OH | X01977 | |
| I-Csm I | Chlamydomonas smithii | 237 | | | | X55305 | |
| I-Dir I | Didymium iridis (Pan 2) | 244 | | | | X71792 | |
| I-Dmo I | Desulfurococcus mobilis | 194 | | rare | 4'/3'OH | P21505 | |
| I-Hmu I | Bacteriophage SPO1/B. subtilis | 174 | | | | M37686 | |
| I-Hmu II | Bacteriophage SP82/B. subtilis | 187 | | | | | |
| I-Ppo I | Physarum polycephalum (Carolina) | 185 | 15 | rare | 4'/3'OH | M38131 | Yes |
| I-Sce I | Saccharomyces cerevisiae (IL8-8C/R53) | 235 | 18 | very rare | 4'/3'OH | P03882 | Yes |
| I-Sce II | Saccharomyces cerevisiae (D273-10B) | 316 | 15 | frequent | 4'/3'OH | P03878 | |
| I-Sce III | Saccharomyces cerevisiae (777-3A) | 335 | 18 | very rare | 4'/3'OH | P03877 | |
| I-Sce IV | Saccharomyces cerevisiae (777-3A) | 307 | | rare | 4'/3'OH | | |
| I-Tev I | Bacteriophage T4/E. coli | 245 | 39 | ? | 2'/3'OH | M12742 | |
| I-Tev II | Bacteriophage T4/E. coli | 258 | 25 | ? | 2'/3'OH | | |
| I-Tev III | Bacteriophage RB3/E. coli | 269 | | | 2'/5'P | X59078 | |
| INTERCALATING PROTEINS | | | | | | | |
| PI-Mle I | Mycobacterium leprae | 365 | | | | X73822 | |
| PI-Mtu I | Mycobacterium tuberculosis | 439 | | | | X58485 | |
| PI-Psp I | Pyrococcus species (GB-D) | 537 | | | | U00707 | |
| PI-Tli I | Thermococcus litoralis | 390 | 20 | rare | 4'/3'OH | M74198 | Yes |
| PI-Tli II | Thermococcus litoralis | 541 | 12 | very rare | 4'/3'OH | M74198 | Yes |
| PI-Sce V | Saccharomyces cerevisiae (YFG 499) | 454 | 12 | very rare | 4'/3'OH | M21609 | Yes |

FIG. 3

GENE REPAIR INVOLVING IN VIVO EXCISION OF TARGETING DNA

RELATED APPLICATIONS

This application is a continuation of U.S. application Ser. No. 10/336,069, filed on Jan. 2, 2003 now U.S. Pat. No. 7,285,538, which is a continuation of U.S. application Ser. No. 09/922,495, filed on Aug. 3, 2001 now abandoned, which is a continuation of International Application No. PCT/US00/02949, which designated the United States and was filed on Feb. 3, 2000, published in English, which claims the benefit of U.S. Provisional Application No. 60/118,472, filed Feb. 3, 1999. The entire teachings of these applications are incorporated herein by reference.

BACKGROUND OF THE INVENTION

Homologous recombination and, more specifically D-loop mediated recombination, provide a method for genetically modifying chromosomal DNA sequences in a precise way. In addition to the possibility of introducing small precise mutations in order to alter the activity of the chromosomal DNA sequences, such a methodology makes it possible to correct the genetic defects in genes which can cause disease. Unfortunately, current methods for achieving homologous recombination are inherently inefficient, in that homologous recombination or D-loop recombination-mediated gene repair can usually be achieved in only a small proportion of cells that have taken up the relevant "targeting or correcting" DNA. For example, in cultured mammalian cells, such recombinational events usually occur in only one in ten thousand cells which have taken up the relevant targeting or correcting DNA. Accordingly, the use of biochemical selections are normally necessary to identify and isolate cells which have successfully recombined input DNA.

Thus, there is a need to develop new and improved methods of homologous recombination or D-loop recombination-mediated gene repair.

SUMMARY OF THE INVENTION

The present invention is related to Applicants' discovery that excision of targeting or correcting DNA from a vector within cells which have taken up the vector significantly increased the frequency of homologous recombination and D-loop recombination-mediated gene repair in these cells. As a result, Applicants' invention relates to methods which result in excision of targeting or correcting DNA from a vector within cells which have taken up the vector. The methods comprise introducing into a cell (a) a first vector which comprises a targeting DNA, wherein the targeting DNA comprises DNA homologous to a chromosomal target site and is flanked by specific restriction endonuclease site(s), and (b) a restriction endonuclease which cleaves the restriction endonuclease site(s) and is present in the first vector or a second (separate) vector which comprises a nucleic acid encoding the restriction endonuclease or is introduced as the restriction endonuclease itself. In one embodiment, two vectors are introduced into cells: a first vector which comprises a targeting DNA, wherein the targeting DNA comprises DNA homologous to a chromosomal target site and is flanked by specific restriction endonuclease sites and a second vector which comprises a nucleic acid (e.g., DNA) which encodes the restriction endonuclease. Alternatively, a single vector which comprises both targeting DNA, wherein the targeting DNA comprises DNA homologous to a chromosomal, target site and is flanked by specific restriction endonuclease site(s), and a nucleic acid encoding a restriction endonuclease which cleaves the restriction endonuclease site(s), is introduced into the cell. In the embodiments described herein, the targeting DNA is flanked by a restriction endonuclease site if such a site is present at or near either or both ends of the targeting DNA. That is, there can be one restriction endonuclease site present at or near one end of the targeting DNA or there can be two such sites, one at or near each end of the targeting DNA. The restriction endonuclease site(s) are recognized (cleaved) by the restriction endonuclease used in the method. As described below, the endonuclease used in the method is one whose activity does not lead to the death of cells in which it cleaves. One example of an endonuclease useful in the method is a meganuclease enzyme. Two (or more) different restriction endonucleases can be used in the present method.

The present invention relates to a method of repairing a specific sequence of interest in chromosomal DNA of a cell comprising introducing into the cell (a) a vector comprising targeting DNA, wherein the targeting DNA is flanked by a restriction endonuclease site or sites and comprises (1) DNA homologous to chromosomal DNA adjacent to the specific sequence of interest and (2) DNA which repairs the specific sequence of interest upon recombination between the targeting DNA and the chromosomal DNA, and (b) a restriction endonuclease which cleaves the restriction endonuclease site(s) present in the vector. The two can be introduced, as described above, in the same or separate vectors or a vector comprising targeting DNA flanked by specific restriction endonuclease site(s) and the endonuclease itself (not in a vector) can be introduced. Preferably, the targeting DNA is flanked by two restriction endonuclease sites. Typically, the targeting DNA is designed such that the homologous DNA is at the left and right arms of the targeting DNA construct and DNA which repairs the specific sequence of interest is inserted between the two arms. In another embodiment of this method, the restriction endonuclease is introduced into the cell by introducing into the cell a second vector which comprises a nucleic acid encoding a restriction endonuclease which cleaves the restriction endonuclease site(s) present in the vector. In yet another embodiment of this method, both targeting DNA and nucleic acid encoding the restriction endonuclease which cleaves the specific sites present in the vector are introduced into the cell in the same vector. As used herein, chromosomal DNA adjacent to a specific sequence of interest refers to chromosomal DNA present near or next to the specific sequence of interest.

In a particular embodiment, the specific sequence of interest is a mutation.

The present invention also relates to a method of modifying a specific sequence (or gene) in chromosomal DNA of a cell comprising introducing into the cell (a) a vector comprising targeting DNA, wherein the targeting DNA is flanked by a restriction endonuclease site and comprises (1) DNA homologous to the specific sequence (or gene) to be modified and (2) DNA which results in modification of the specific sequence (or gene) upon recombination between the targeting DNA and the chromosomal DNA, and (b) a restriction endonuclease which cleaves the restriction endonuclease site present in the vector. Preferably, the targeting DNA is flanked by two restriction endonuclease sites (one at or near each end of the targeting DNA). Typically, the targeting DNA is designed such that the homologous DNA is at the left and right arms of the targeting DNA construct and DNA which results in modification of the specific sequence (or gene) is inserted between the two arms. In another embodiment of this method, the restriction endonuclease is introduced into the cell by introducing into the cell a second vector (either RNA or DNA) which comprises a nucleic acid encoding the restriction endonuclease. In yet another embodiment of this method, both targeting DNA and nucleic acid encoding the restriction endonuclease are introduced into the cell in the same vector.

The invention further relates to a method of attenuating an endogenous gene of interest in a cell comprising introducing into the cell (a) a vector comprising targeting DNA, wherein the targeting DNA is flanked by a restriction endonuclease site and comprises (1) DNA homologous to a target site of the endogenous gene of interest and (2) DNA which attenuates the gene of interest upon recombination between the targeting DNA and the gene of interest, and (b) a restriction endonuclease which cleaves the restriction endonuclease site present in the vector. Preferably, the targeting DNA is flanked by two restriction endonuclease sites. Typically, the targeting DNA is designed such that the homologous DNA is at the left and right arms of the targeting DNA construct and DNA which attenuates the gene of interest is located between the two arms. In another embodiment of this method, the restriction endonuclease is introduced into the cell by introducing into the cell a second vector (either RNA or DNA) which comprises a nucleic acid encoding the restriction endonuclease. In yet another embodiment of this method, both targeting DNA and nucleic acid encoding the restriction endonuclease are introduced into the cell in the same vector.

The present invention also relates to a method of introducing a mutation into a target site of chromosomal DNA of a cell comprising introducing into the cell (a) a first vector comprising targeting DNA, wherein the targeting DNA is flanked by a restriction endonuclease site and comprises (1) DNA homologous to the target site and (2) the mutation to be introduced into the chromosomal DNA, and (b) a second vector (RNA or DNA) comprising a nucleic acid encoding a restriction endonuclease which cleaves the restriction endonuclease site present in the first vector. Preferably, the targeting DNA is flanked by two restriction endonuclease sites. Typically, the targeting DNA is designed such that the homologous DNA is at the left and right arms of the targeting DNA construct and the mutation is located between the two arms. In another embodiment of this method, the restriction endonuclease is introduced directly into the cell. In yet another embodiment of this method, both targeting DNA and nucleic acid encoding a restriction endonuclease which cleaves the restriction endonuclease site are introduced into the cell in the same vector.

The present invention also relates to the resulting cells and to their uses, such as for production of proteins or other gene products or for treatment or prophylaxis of a condition or disorder in an individual (e.g., a human or other mammal or vertebrate) arising as a result of a genetic defect (mutation). For example, cells can be produced (e.g., ex vivo) by the methods described herein and then introduced into an individual using known methods. Alternatively, cells can be modified in the individual (without being removed from the individual).

Thus, the invention further relates to a method of treating or prophylaxis of a genetic disease in an individual in need thereof. In one embodiment, this method comprises introducing into the individual cells which comprise (a) a first vector comprising targeting DNA, wherein the targeting DNA is flanked by a restriction endonuclease site or sites and comprises (1) DNA homologous to chromosomal DNA adjacent to a specific sequence of interest and (2) DNA which repairs the specific sequence of interest upon recombination between the targeting DNA and the chromosomal DNA, and (b) a second vector (RNA or DNA) comprising a nucleic acid encoding a restriction endonuclease which cleaves the restriction endonuclease site(s) present in the first vector. In a second embodiment, this method comprises introducing into the individual cells which comprise (a) a vector comprising targeting DNA, wherein the targeting DNA is flanked by a restriction endonuclease site(s) and comprises (1) DNA homologous to chromosomal DNA and (2) DNA which repairs the specific sequence of interest upon recombination between the targeting DNA and the chromosomal DNA, and (b) a restriction endonuclease which cleaves the restriction endonuclease site present in the vector. In a third embodiment, this method comprises introducing into the individual cells which comprise a vector comprising (a) targeting DNA, wherein the targeting DNA is flanked by a restriction endonuclease site(s) and comprises (1) DNA homologous to chromosomal DNA and (2) DNA which repairs the specific sequence of interest upon recombination between the targeting DNA and the chromosomal DNA, and (b) nucleic acid encoding a restriction endonuclease which cleaves the restriction endonuclease site present in the plasmid. Preferably, the targeting DNA is flanked by two restriction endonuclease sites. Typically, the targeting DNA is designed such that the homologous DNA is at the left and right arms of the targeting DNA construct and DNA which repairs the specific sequence of interest is located between the two arms.

Alternatively, in a method of treating or prophylaxis of a genetic disease in an individual in need thereof, restriction endonucleases and vectors comprising targeting DNA and/or nucleic acid encoding a restriction endonuclease can be administered directly to the individual.

BRIEF DESCRIPTION OF THE DRAWINGS

FIG. 2 is a table which provides the results from I-SceI induced D-loop recombination-mediated repair experiments in NIH3T3 cells.

FIG. 3 is a table providing examples of meganuclease enzymes.

DETAILED DESCRIPTION OF THE INVENTION

Figure 1:
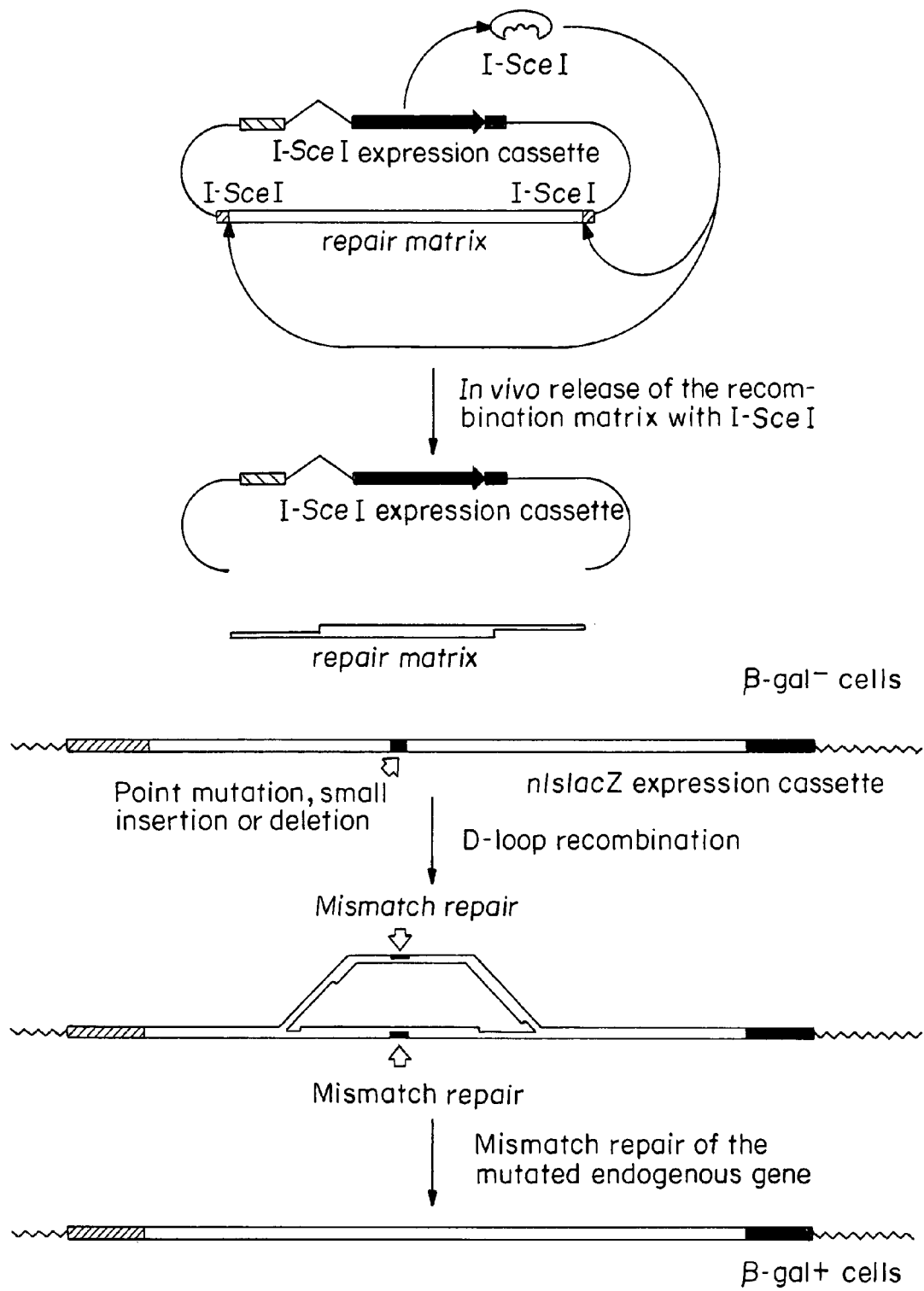
FIG. 1 is a schematic diagram of an embodiment of a homologous recombination or D-loop recombination-mediated repair method described herein.

The present invention relates to the development of a generally useful method for significantly increasing the frequency of homologous recombination and D-loop recombination-mediated gene repair. At least in vitro, over 1% of a population of transfected cells can be shown to generate the desired recombinational events using the methods described herein. It is likely that these findings represent the ability to achieve homologous recombination and/or gene repair in close to 10% of successfully transfected cells (or higher) when corrected for the efficiency of transfection (the percent cells that take up DNA).

The invention relates to the use of methods which lead to the excision of homologous targeting DNA sequences from a recombinant vector within transfected cells (cells which have taken up the vector). The methods comprise introducing into cells (a) a first vector which comprises a targeting DNA, wherein the targeting DNA flanked by specific restriction endonuclease site(s) and comprises DNA homologous to a chromosomal target site, and (b) a restriction endonuclease which cleaves the restriction endonuclease site(s) present in the first vector or a second vector which comprises a nucleic acid encoding the restriction endonuclease. Alternatively, a vector which comprises both targeting DNA and a nucleic acid encoding a restriction endonuclease which cleaves the restriction endonuclease site(s) is introduced into the cell. Nucleic acid encoding the restriction endonuclease is also referred to herein as an expression cassette encoding the restriction endonuclease. Targeting DNA is also referred to herein as a repair matrix and correcting DNA.

In the embodiments described herein, the targeting DNA is flanked by a restriction endonuclease site if such a site is present at or near either or both ends of the targeting DNA. That is, there can be one restriction endonuclease site present at or near one end of the targeting DNA or there can be two such sites, one at or near each end of the targeting DNA.

A restriction endonuclease used in the present invention recognizes a target DNA sequence (e.g., a restriction endonuclease site) which would not lead to death of the cells upon cleavage of the DNA sequence by the restriction endonuclease. A meganuclease enzyme, which recognizes a very large DNA sequence, is an example of a restriction endonuclease which can be used in the present invention. An example of a meganuclease enzyme is I-SceI which recognizes an 18-bp site (DNA sequence) that does not appear to be represented in murine or human DNA. Other examples of meganuclease enzymes are provided in FIG. 3. Other meganuclease enzymes (natural and synthetic) are known and described in the art. In a particular embodiment, a restriction endonuclease used in the present invention has a specificity of at least $6.7 \times 10^{-10}$ of cleaving (cutting) frequency.

Expression of commonly used four and six base cutting restriction enzymes within cells would usually lead to cleavage of chromosomal DNA and death of the cells due to the existence of many restriction sites within the cellular DNA which are recognized by the enzymes. Accordingly, such restriction enzymes are not used in the present invention.

The excision of a linear segment of DNA within cells (presumably within the nucleus) appears to generate a form of DNA which can be more efficiently utilized for recombination than either circular DNA or DNA linearized in vitro (prior to transfection) that are introduced into cells. This may relate to the generation of a linear segment of DNA that is either more resistant to exonucleolytic degradation than linear DNA that is transfected, or perhaps to the generation of a template more capable of forming complexes with gene products essential for recombinational event.

The ability to achieve homologous recombination and gene repair at high efficiency allows for the treatment of genetic diseases by true gene repair, rather than by the addition of a functional gene to genes, as is currently the major focus of gene therapy. The method described herein should not require long term expression of introduced DNA in vivo, a common problem with current gene therapy experiments, since only the transient expression of the appropriate restriction endonuclease should be necessary to excise the 'correcting' linear segment of DNA.

The present invention relates to a method of repairing a specific sequence of interest in chromosomal DNA of a cell comprising introducing into the cell (a) a vector comprising targeting DNA, wherein the targeting DNA is flanked by a restriction endonuclease site or sites and comprises (1) DNA homologous to chromosomal DNA adjacent to the specific sequence of interest and (2) DNA which repairs the specific sequence of interest upon recombination between the targeting DNA and the chromosomal DNA, and (b) a restriction endonuclease which cleaves the restriction endonuclease site(s) present in the vector. Preferably, the targeting DNA is flanked by two restriction endonuclease sites (one at or near each end of the targeting DNA). In another embodiment of this method, the restriction endonuclease is introduced into the cell by introducing into the cell a second vector which comprises a nucleic acid encoding a restriction endonuclease which cleaves the restriction endonuclease site(s) present in the vector. In yet another embodiment of this method, both targeting DNA and nucleic acid encoding the restriction endonuclease are introduced into the cell in the same vector.

In a method of repairing a specific sequence of interest in chromosomal DNA of a cell, the targeting DNA is designed such that homologous recombination, and more preferably, D-loop mediated recombination, occurs between the targeting DNA and chromosomal DNA and, upon recombination, repair of the specific sequence of interest occurs. Thus, in a particular embodiment, the targeting DNA is designed to include (1) DNA homologous to chromosomal DNA adjacent to the specific sequence of interest, wherein the homologous DNA is sufficient for recombination between the targeting DNA and chromosomal DNA, and (2) DNA which repairs the specific sequence of interest upon recombination between the targeting DNA and chromosomal DNA. Typically, the homologous DNA of the targeting DNA construct flanks each end of the DNA which repairs the specific sequence of interest. That is, the homologous DNA is at the left and right arms of the targeting DNA construct and the DNA which repairs the sequence of interest is located between the two arms.

In a particular embodiment, the specific sequence of interest is a mutation. Thus, in this embodiment, the invention relates to a method of repairing a mutation in chromosomal DNA of a cell comprising introducing into the cell (a) a vector comprising targeting DNA wherein the targeting DNA is flanked by a restriction endonuclease site or sites and comprises (1) DNA homologous to chromosomal DNA adjacent to the mutation and (2) DNA which repairs the mutation upon recombination between the targeting DNA and the chromosomal DNA, and (b) a restriction endonuclease which cleaves the restriction endonuclease site(s) present in the vector. Preferably, the targeting DNA is flanked by two restriction endonuclease sites (one at or near each end of the targeting DNA). In another embodiment of this method, the restriction endonuclease is introduced into the cell by introducing into the cell a second vector which comprises a nucleic acid encoding a restriction endonuclease which cleaves the restriction endonuclease site(s) present in the vector. In yet another embodiment of this method, both targeting DNA and nucleic acid encoding the restriction endonuclease are introduced into the cell in the same vector.

In a method of repairing a mutation in chromosomal DNA of a cell, the targeting DNA is designed such that homologous recombination, and more preferably, D-loop mediated recombination, occurs between the targeting DNA and chromosomal DNA and, upon recombination, repair of the mutation occurs. Thus, in a particular embodiment, the targeting DNA is designed to include (1) DNA homologous to chromosomal DNA adjacent to the mutation, wherein the homologous DNA is sufficient for recombination between the targeting DNA and chromosomal DNA, and (2) DNA which repairs the mutation upon recombination between the targeting DNA and chromosomal DNA. Typically, the homologous DNA of the targeting DNA construct flanks each end of the DNA which repairs the mutation. That is, the homologous DNA is at the left and right arms of the targeting DNA construct and the DNA which repairs the mutation is located between the two arms.

As used herein, a mutation refers to a nucleotide change, such as a single or multiple nucleotide substitution, deletion or insertion, in a nucleotide sequence. Preferably, the mutation is a point mutation. Chromosomal DNA which bears a mutation has a nucleic acid sequence that is different in sequence from that of the corresponding wildtype chromosomal DNA.

As used herein, chromosomal DNA adjacent to a specific sequence of interest refers to chromosomal DNA present near or next to the specific sequence of interest.

The present invention also relates to a method of modifying a specific sequence (or gene) in chromosomal DNA of a cell comprising introducing into the cell (a) a vector comprising targeting DNA, wherein the targeting DNA is flanked by a restriction endonuclease site and comprises (1) DNA homologous to the specific sequence (or gene) to be modified and (2) DNA which modifies the specific sequence (or gene) upon recombination between the targeting DNA and the chromosomal DNA, and (b) a restriction endonuclease which cleaves the restriction endonuclease site present in the vector. Preferably, the targeting DNA is flanked by two restriction endonuclease sites. In another embodiment of this method, the restriction endonuclease is introduced into the cell by introducing into the cell a second vector (either RNA or DNA) which comprises a nucleic acid encoding the restriction endonuclease. In yet another embodiment of this method, both targeting DNA and nucleic acid encoding the restriction endonuclease are introduced into the cell in the same vector.

In a method of modifying a specific sequence (or gene) in chromosomal DNA of a cell, the targeting DNA is designed such that homologous recombination, and more preferably, D-loop mediated recombination, occurs between the targeting DNA and chromosomal DNA and, upon recombination, modification of the sequence (or gene) occurs. Thus, in a particular embodiment, the targeting DNA is designed to include (1) DNA homologous to the specific sequence (or gene) to be modified, wherein the homologous DNA is sufficient for recombination between the targeting DNA and chromosomal DNA, and (2) DNA which modifies the specific sequence (or gene) upon recombination between the targeting DNA and the chromosomal DNA. Typically, the homologous DNA of the targeting DNA construct flanks each end of the DNA which modifies the specific sequence (or gene). That is, the homologous DNA is at the left and right arms of the targeting DNA construct and the DNA which modifies the specific sequence (or gene) is located between the two arms.

The invention further relates to a method of attenuating or inactivating an endogenous gene of interest in a cell comprising introducing into the cell (a) a vector comprising targeting DNA, wherein the targeting DNA is flanked by a restriction endonuclease site and comprises (1) DNA homologous to a target site of the endogenous gene of interest and (2) DNA which attenuates or inactivates the gene of interest upon recombination between the targeting DNA and the gene of interest, and (b) a restriction endonuclease which cleaves the restriction endonuclease site present in the vector. Preferably, the targeting DNA is flanked by two restriction endonuclease sites, as described above. In another embodiment of this method, the restriction endonuclease is introduced into the cell by introducing into the cell a second vector (either RNA or DNA) which comprises a nucleic acid encoding the restriction endonuclease. In yet another embodiment of this method, both the targeting DNA and the nucleic acid encoding the restriction endonuclease are introduced into the cell in the same vector.

In a method of attenuating or inactivating an endogenous gene of interest in a cell, the targeting DNA is designed such that homologous recombination, and more preferably, D-loop mediated recombination, occurs between the targeting DNA and endogenous gene of interest and, upon recombination, attenuation or inactivation of the gene of interest occurs.

Thus, in a particular embodiment, the targeting DNA is designed to include (1) DNA homologous to a target site of the endogenous gene of interest, wherein the homologous DNA is sufficient for recombination between the targeting DNA and the gene of interest, and (2) DNA which attenuates or inactivates the gene of interest upon recombination between the targeting DNA and the gene of interest. Typically, the homologous DNA of the targeting DNA construct flanks each end of the DNA which attenuates or inactivates the gene of interest. That is, the homologous DNA is at the left and right arms of the targeting DNA construct and the DNA which attenuates or inactivates the gene of interest is located between the two arms.

The present invention also relates to a method of introducing a mutation into a target site (or gene) of chromosomal DNA of a cell comprising introducing into the cell (a) a first vector comprising targeting DNA, wherein the targeting DNA is flanked by a restriction endonuclease site and comprises (1) DNA homologous to the target site (or gene) and (2) the mutation to be introduced into the chromosomal DNA, and (b) a second vector (RNA or DNA) comprising a nucleic acid encoding a restriction endonuclease which cleaves the restriction endonuclease site present in the first vector. Preferably, the targeting DNA is flanked by two restriction endonuclease sites. In another embodiment of this method, the restriction endonuclease is introduced directly into the cell. In yet another embodiment of this method, both targeting DNA and nucleic acid encoding a restriction endonuclease which cleaves the restriction endonuclease site, are introduced into the cell in the same vector.

In a method of introducing a mutation into a target site (or gene) of chromosomal DNA of a cell, the targeting DNA is designed such that homologous recombination, and more preferably, D-loop mediated recombination, occurs between the targeting DNA and the chromosomal DNA and, upon recombination, a mutation is introduced into the target site (or gene). Thus, in a particular embodiment, the targeting DNA is designed to include (1) DNA homologous to the target site (or gene), wherein the homologous DNA is sufficient for recombination between the targeting DNA and the chromosomal DNA, and (2) the mutation which is introduced into the chromosomal DNA upon recombination between the targeting DNA and the chromosomal DNA. Typically, the homologous DNA of the targeting DNA construct flanks each end of the mutation. That is, the homologous DNA is at the left and right arms of the targeting DNA construct and the mutation to be introduced into the chromosomal DNA (i.e., into a target site or gene) is located between the two arms.

The invention further relates to a method of treating or prophylaxis of a genetic disease in an individual in need thereof. As used herein, a genetic disease refers to a disease or disorder that arises as a result of a genetic defect (mutation) in a gene in the individual. In a particular embodiment, the genetic disease arises as a result of a point mutation in a gene in the individual.

In one embodiment, the method of treating or prophylaxis of a genetic disease in an individual in need thereof comprises introducing into (administering to) the individual cells which comprise (a) a first vector comprising targeting DNA, wherein the targeting DNA is flanked by a restriction endonuclease site and comprises (1) DNA homologous to chromosomal DNA adjacent to a specific sequence of interest and (2) DNA which repairs the specific sequence of interest upon recombination between the targeting DNA and the chromosomal DNA, and (b) a second vector (RNA or DNA) comprising a nucleic acid encoding a restriction endonuclease which cleaves the restriction endonuclease site present in the first vector. In a second embodiment, the method comprises introducing into the individual cells which comprise (a) a vector comprising targeting DNA, wherein the targeting DNA is flanked by a restriction endonuclease site and comprises (1) DNA homologous to chromosomal DNA adjacent to a specific sequence of interest (2) DNA which repairs the specific sequence of interest upon recombination between the targeting DNA and the chromosomal DNA, and (b) a restriction endonuclease which cleaves the restriction endonuclease site present in the vector. In a third embodiment, the method comprises introducing into the individual cells which comprise a vector comprising (a) targeting DNA, wherein the targeting DNA is flanked by a restriction endonuclease site and comprises (1) DNA homologous to chromosomal DNA adjacent to a specific sequence of interest and (2) DNA which repairs the specific sequence of interest upon recombination between the targeting DNA and the chromosomal DNA, and (b) nucleic acid encoding a restriction endonuclease which cleaves the restriction endonuclease site present in the plasmid. Preferably, the targeting DNA is flanked by two restriction endonuclease sites. Typically, the homologous DNA of the targeting DNA construct flanks each end of the DNA which repairs the specific sequence of interest. That is, the homologous DNA is at the left and right arms of the targeting DNA construct and the DNA which repairs the sequence of interest is located between the two arms.

Alternatively, in a method of treating or prophylaxis of a genetic disease in an individual in need thereof, restriction endonucleases and vectors comprising targeting DNA and/or nucleic acid encoding a restriction endonuclease can be administered directly to the individual. The mode of administration is preferably at the location of the target cells. In one embodiment, the method comprises introducing into (administering to) the individual (a) a first vector comprising targeting DNA, wherein the targeting DNA is flanked by a restriction endonuclease site and (1) DNA homologous to chromosomal DNA adjacent to a specific sequence of interest and (2) DNA which repairs the specific sequence of interest upon recombination between the targeting DNA and the chromosomal DNA, and (b) a second vector (RNA or DNA) comprising a nucleic acid encoding a restriction endonuclease which cleaves the restriction endonuclease site present in the first vector. In a second embodiment, the method comprises introducing into the individual (a) a vector comprising targeting DNA, wherein the targeting DNA is flanked by a restriction endonuclease site and (1) DNA homologous to chromosomal DNA adjacent to a specific sequence of interest and (2) DNA which repairs the specific sequence of interest upon recombination between the targeting DNA and the chromosomal DNA, and (b) a restriction endonuclease which cleaves the restriction endonuclease site present in the vector. In a third embodiment, the method comprises introducing into the individual a vector comprising (a) targeting DNA, wherein the targeting DNA is flanked by a restriction endonuclease site and (1) DNA homologous to chromosomal DNA adjacent to a specific sequence of interest and DNA which repairs the specific sequence of interest upon recombination between the targeting DNA and the chromosomal DNA, and (b) nucleic acid encoding a restriction endonuclease which cleaves the restriction endonuclease site present in the plasmid. Preferably, the targeting DNA is flanked by two restriction endonuclease sites.

The invention also relates to the generation of animal models of disease in which restriction endonuclease sites (e.g., I-SceI target sites) are introduced at the site of the disease gene for evaluation of optimal delivery techniques.

The efficiency of gene modification/repair can be enhanced by the addition expression of other gene products. The restriction endonuclease and other gene products can be directly introduced into a cell in conjunction with the correcting DNA or via RNA expression. The approach is applicable to all organisms.

Targeting DNA can be manufactured according to methods generally known in the art. For example, targeting DNA can be manufactured by chemical synthesis or recombinant DNA/RNA technology (see, e.g., Sambrook et al., Eds., *Molecular Cloning: A Laboratory Manual*, 2nd edition, Cold Spring Harbor University Press, New York (1989); and Ausubel et al., Eds., *Current Protocols In Molecular Biology*, John Wiley & Sons, New York (1997)).

A "target site", as used herein, refers to a distinct chromosomal location at which a chromosomal DNA sequence is to be modified in a precise way in accordance with the methods described herein.

As used herein, a "vector" includes a nucleic acid vector, e.g., a DNA vector, such as a plasmid, a RNA vector, virus or other suitable replicon (e.g., viral vector).

Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, *In Fundamental Virology*, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

A vector comprising a nucleic acid encoding a restriction endonuclease contains all or part of the coding sequence for the restriction endonuclease operably linked to one or more expression control sequences whereby the coding sequence is under the control of transcription signals to permit production or synthesis of the restriction endonuclease. Such expression control sequences include promoter sequences, enhancers, and transcription binding sites. Selection of the promoter will generally depend upon the desired route for expressing the restriction endonuclease. The elements can be isolated from nature, modified from native sequences or manufactured de novo (e.g., by chemical synthesis or recombinant DNA/RNA technology, according to methods known in the art (see, e.g., Sambrook et al., Eds., *Molecular Cloning: A Laboratory Manual*, 2nd edition, Cold Spring Harbor University Press, New York (1989); and Ausubel et al., Eds., *Current Protocols In Molecular Biology*, John Wiley & Sons, New York (1997)). The elements can then be isolated and fused together by methods known in the art, such as exploiting and manufacturing compatible cloning or restriction sites.

Similarly, a vector comprising targeting DNA flanked by a restriction endonuclease site can be manufactured according to methods generally known in the art. For example, the vector comprising targeting DNA flanked by a restriction endonuclease site can be manufactured by chemical synthesis or recombinant DNA/RNA technology (see, e.g., Sambrook et al., Eds., *Molecular Cloning, A Laboratory Manual*, 2nd edition, Cold Spring Harbor University Press, New York, 1989; and Ausubel et al., Eds., *Current Protocols In Molecular Biology*, John Wiley & Sons, New York, 1994-1997).

Vectors comprising targeting DNA flanked by a restriction endonuclease site and/or nucleic acid encoding a restriction endonuclease can be introduced into a cell by a variety of methods (e.g., transformation, transfection, direct uptake, projectile bombardment, using liposomes). Examples of suitable methods of transfecting or transforming cells include calcium phosphate precipitation, electroporation, microinjection, infection, lipofection and direct uptake. Such methods are described in more detail, for example, in Sambrook et al., *Molecular Cloning: A Laboratory Manual*, Second Edition, Cold Spring Harbor University Press, New York (1989); and Ausubel, et al., *Current Protocols in Molecular Biology*, John Wiley & Sons, New York (1998), the teachings of which are incorporated herein by reference.

A vector comprising targeting DNA flanked by a restriction endonuclease site and/or nucleic acid encoding a restriction endonuclease can also be introduced into a cell by targeting the vector to cell membrane phospholipids. For example, targeting of a vector of the present invention can be accomplished by linking the vector molecule to a VSV-G protein, a viral protein with affinity for all cell membrane phospholipids. Such a construct can be produced using methods well known to those practiced in the art.

Restriction endonucleases can be introduced into a cell according to methods generally known in the art which are appropriate for the particular restriction endonuclease and cell type. For example, a restriction endonuclease can be introduced into a cell by direct uptake, microinjection, calcium phosphate precipitation, electroporation, infection, and lipofection. Such methods are described in more detail, for example, in Sambrook et al., *Molecular Cloning: A Laboratory Manual*, Second Edition, Cold Spring Harbor University Press, New York (1989); and Ausubel, et al., *Current Protocols in Molecular Biology*, John Wiley & Sons, New York (1998). Other suitable methods are also described in the art. The restriction endonuclease can be coupled to a facilitator of protein entry to facilitate introduction of the enzyme into a cell. Examples of facilitators of protein entry include tat, HSV VP22 and anthrax toxin. Coupling of a protein to a facilitator of protein entry can be accomplished using methods well known to those practiced in the art. Protein delivery strategies (e.g., HSV VP22, anthrax toxin) can be evaluated in accordance with the methods of the invention described herein.

Once in the cell, the restriction endonuclease and the vector comprising targeting DNA flanked by a restriction endonuclease site and/or nucleic acid encoding a restriction endonuclease are imported or translocated by the cell from the cytoplasm to the site of action in the nucleus.

As used herein, a cell refers to a prokaryotic cell, such as a bacterial cell, or eukaryotic cell, such as an animal, plant or yeast cell. A cell which is of animal or plant origin can be a stem cell or somatic cell. Suitable animal cells can be of, for example, mammalian, avian or invertebrate origin. Examples of mammalian cells include human (such as HeLa cells), bovine, ovine, porcine, murine (such as embryonic stem cells), rabbit and monkey (such as COS 1 cells) cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

The cells can be obtained commercially or from a depository or obtained directly from an individual, such as by biopsy. The cells used can be obtained from an individual to whom they will be returned or from another/different individual of the same or different species. For example, nonhuman cells, such as pig cells, can be modified to include a DNA construct and then introduced into a human. Such a treating procedure is sometimes referred to as ex vivo treatment. Ex vivo therapy has been described, for example, in Kasid et al., *Proc. Natl. Acad. Sci. USA*, 87:473 (1990); Rosenberg et al., *N. Engl. J. Med.*, 323:570 (1990); Williams et al., *Nature*, 310:476 (1984); Dick et al., *Cell*, 42:71 (1985); Keller et al., *Nature*, 318:149 (1985); and Anderson et al., U.S. Pat. No. 5,399,346. Alternatively, the cells need not be isolated from the individual where, for example, it is desirable to deliver the vector to the individual in gene therapy.

As used herein, the term "individual" includes mammals, as well as other animals (e.g., birds, fish, reptiles, insects). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and other primates (e.g., monkeys, chimpanzees), rodents (e.g., rats, mice, guinea pigs) and ruminants (e.g., cows, pigs, horses).

Restriction endonucleases and vectors which comprise targeting DNA flanked by a restriction endonuclease site and/or nucleic acid encoding a restriction endonuclease can be introduced into an individual using routes of administration generally known in the art (e.g., parenteral, mucosal, nasal, injection, systemic, implant, intraperitoneal, oral, intradermal, transdermal (e.g., in slow release polymers), intramuscular, intravenous including infusion and/or bolus injection, subcutaneous, topical, epidural, buccal, rectal, vaginal, etc.). The restriction endonucleases and vectors can, preferably, be administered in a pharmaceutically acceptable carrier, such as saline, sterile water, Ringer's solution, and isotonic sodium chloride solution. The mode of administration is preferably at the location of the target cells.

The dosage of restriction endonuclease or vector of the present invention administered to an individual, including frequency of administration, will vary depending upon a variety of factors, including mode and route of administration; size, age, sex, health, body weight and diet of the recipient; nature and extent of symptoms of the disease or disorder being treated; kind of concurrent treatment, frequency of treatment, and the effect desired.

The present invention will now be illustrated by the following examples, which are not to be considered limiting in any way.

EXAMPLES

Example 1

Plasmid Construction

All DNA manipulations used standard techniques and procedures. Such methods are described, for example, in Sambrook et al., *Molecular Cloning: A Laboratory Manual*, Second Edition, Cold Spring Harbor University Press, New York (1989); and Ausubel, et al., *Current Protocols in Molecular Biology*, John Wiley & Sons, New York (1998). All synthetic oligonucleotides were synthesized on automated instruments using standard techniques.

The p2Wlac plasmid was constructed as follows: First, the pPytknlslacZ plasmid (Henry et al., *C. R. Acad. Sci. III*, 322(12):1061-1070 (1999)) was digested with the SpeI and HindIII restriction enzymes, resulting in excision from the plasmid of a 578 bp fragment containing the ATG start codon and 178 bp at the 5' end of the coding region of the nlslacZ gene. Second, the oligonucleotide 5'-CTAGATGCATAGG-GATAACAGGGTAAT-3' (SEQ ID NO: 1), paired with 5'-AGCTATTACCCTGTTATCCCTATGCAT-3' (SEQ ID NO:2), was inserted into the SpeI-Hind III restriction sites of the pPytknlslacZ plasmid (Henry et al., *C. R. Acad. Sci. III*, 322(12):1061-1070 (1999)) to produce the pWnlslacZ plasmid. Insertion of the oligonucleotide at the SpeI-Hind III restriction sites resulted in destruction of the SpeI and HindIII restriction sites and insertion of a NsiI restriction site and an I-SceI restriction site. The pWnlslacZ plasmid was then digested with the NheI and BglII restriction enzymes, resulting in excision from the plasmid of a 0.6 kb fragment containing the stop codon and SV40 polyadenylation signal at the 3' end of the nlslacZ gene. The oligonucleotide 5'-GATCAT-GCATAGGGATAACAGGGTAAT-3' (SEQ ID NO:3), paired with 5'-CTAGATTACCCTGTTATCCCTATGCAT-3' (SEQ ID NO:4), was inserted into the NheI-BglII restriction sites of the pWnlslacZ plasmid. Insertion of the oligonucleotide at the NheI-BglII restriction sites resulted in destruction of the NheI and the BglII restriction sites and insertion of an I-SceI restriction site and a NsiI restriction site. The result of these insertions is the p2Wlac plasmid in which the nlslacZ gene with the ATG start codon, 178 bp at the 5' end, stop codon and SV40 polyadenylation signal deleted, is inserted between two I-SceI sites. As a result of the deletion of the start codon and 178 bp at the 5' end of the coding region, nlslacZ gene expression is inactivated.

The pWlac plasmid was constructed as follows: First, the pPytknlslacZ plasmid was digested with the SpeI and HindIII restriction enzymes, resulting in excision from the plasmid of a 578 bp fragment containing the ATG start codon and 178 bp at the 5' end of the coding region of the nlslacZ gene. Second, the oligonucleotide 5'-CTAGATGCATAGGGATAA-CAGGGTAAT-3' (SEQ ID NO:1), paired with 5'-AGCTAT-TACCCTGTTATCCCTATGCAT-3' (SEQ ID NO:2), was inserted into the SpeI-HindIII restriction sites of the pPytknlslacZ plasmid to produce the pWnlslacZ plasmid. Insertion at this restriction site resulted in destruction of the SpeI and HindIII restriction sites and the insertion of an NsiI restriction site and an I-SceI restriction site. The pWnlslacZ plasmid was digested with the NheI and BglII restriction enzymes, resulting in excision from the plasmid of the 0.6 kb fragment containing the stop codon and SV40 polyadenylation signal at the 3' end of the nlslacZ gene. The 5' extensions of the NheI-BglII restriction sites of the pWnlslacZ plasmid were converted to blunt ends by a filling-in reaction using T4 DNA polymerase. The blunted ends were then ligated together. The result is the pWlac plasmid in which the nlslacZ gene with the ATG start codon, 178 bp at the 5' end, stop codon and SV40 polyadenylation signal deleted, is bounded at the 5' end by one I-SceI site; the 3' end of the nlslacZ gene is not bounded by a I-SceI site. As a result of the deletion of the start codon and 178 bp at the 5' end of the coding region, nlslacZ gene expression is inactivated.

The p-lac plasmid was constructed as follows: First, the pPytknlslacZ plasmid was digested with the SpeI and HindIII restriction enzymes, resulting in excision from the plasmid of a 578 bp fragment containing the ATG start codon and 178 bp at the 5' end of the coding region of the nlslacZ gene. The 5' extensions of the SpeI-HindIII restriction sites of the pPytknlslacZ plasmid were converted to blunt ends by a filling-in reaction using T4 DNA polymerase. The blunted ends were then ligated together to produce the p-lacZ plasmid. The p-lacZ plasmid was digested with the NheI and BglII restriction enzymes, resulting in excision from the plasmid of the 0.6 kb fragment containing the stop codon and SV40 polyadenylation signal at the 3' end of the nlslacZ gene. The 5' extensions of the NheI-BglII restriction sites of the pWnlslacZ plasmid were converted to blunt ends by a filling-in reaction using T4 DNA polymerase. The blunted ends were then ligated together. The result is the p-lac plasmid in which the nlslacZ gene with the ATG start codon, 178 bp at the 5' end, stop codon and SV40 polyadenylation signal deleted, is not bounded at the 5' or 3' end by a I-SceI site. As a result of the deletion of the start codon and 178 bp at the 5' end of the coding region, nlslacZ gene expression is inactivated.

The 2.8 kb linear fragment of the nlslacZ gene used in the experiments described herein was obtained as follows: The pPytknlslacZ plasmid was digested with NheI and HindIII and a 2.8 kb fragment was purified by agarose gel electrophoresis. This 2.8 kb fragment, referred to herein as the lac fragment, contains a fragment of the nlslacZ gene with the ATG start codon, 178 bp at the 5' end, stop codon and SV40 polyadenylation signal deleted.

The pCMV I-SceI(+) and pCMV I-SceI(−) plasmids were described in Choulika et al., *C. R. Acad. Sci. III*, 317(11): 1013-1019 (1994).

The target plasmid pPytknlslacZDBcl was produced by digesting the pPytknlslacZ plasmid with the BclI restriction enzyme after demethylation of the plasmid. The 5' protruding ends were filled-in by the Klenow fragment of *E. coli* DNA polymerase I and religated. The result is insertion of a 4 base pair direct repeat in the sequence of the nlslacZ gene resulting in a frame shift of the open reading frame, thereby inactivating expression of the gene. Thus, the plasmid does not express the β-galactosidase protein.

The target plasmid pPytknlslacZΔBcl was produced by digesting the pPytknlslacZ plasmid with the BclI restriction enzyme after demethylation of the plasmid. The 4 base pair 5' protruding ends were degraded by T4 DNA polymerase and the resulting blunted ends religated. The result is deletion of 4 base pairs within the sequence of the nlslacZ gene resulting in a frame shift of the open reading frame, thereby inactivating expression of the gene. Thus, the plasmid does not express the β-galactosidase protein.

The pUSVneo plasmid was described in Choulika et al., *J. Virol.*, 70(3):1792-1798 (1996).

Example 2

Cell Line Production and D-Loop Recombination: Correction Of A 4 Base Pair Insertion 5 μg of the pPytknlslacZDBcl plasmid and 5 μg of the pUSVneo plasmid were co-transfected into $5 \times 10^4$ NIH 3T3 cells (American Type Culture Collection) in a 35 mm petri dish (Falcon) using the $CaPO_4$ precipitation method. 48 hours after transfection, the tissue culture medium was supplemented with 600 μg/ml of Geneticin (Gibco BRL). Antibiotic selection was maintained during selection of Geneticin resistant clones and during subcloning. Forty-eight (48) Geneticin resistant clones were isolated and grown independently in Dulbeccos modified Eagles Medium (DMEM), 10% calf serum, for 15 days before evaluating for the presence of the nlslacZ gene.

To evaluate for presence of the nlslacZ gene, DNA was extracted from cells in all 48 cultures of Geneticin resistant clones. Fragments of the nlslacZ gene were amplified by polymerase chain reaction (PCR) as described in *BioFeedback in BioTechniques*, Hanley & J. P. Merlie, Vol. 10, No. 1, p. 56T (1991). Forty-six (46) of 48 clones were positive for the presence of the nlslacZ gene.

Twenty-four (24) of the 46 clones positive for the presence of the nlslacZ gene were evaluated for expression of the mutated nlslacZ gene. To evaluate for expression of the mutated nlslacZ gene, RNA was extracted from cells in the corresponding 24 cultures of Geneticin resistant clones. RNA encoding the mutated nlslacZ gene was amplified by reverse transcriptase polymerase chain reaction (RT-PCR). The oligonucleotide primer 5'-TACACGCGTCGTGATTAGCGCCG-3' (SEQ ID NO:5) was used for lacZ reverse transcription. PCR was performed as described in *BioFeedback in BioTechniques*, Hanley & J. P. Merlie, Vol. 10, No. 1, p. 56T (1991). Eleven (11) of 24 clones showed a positive reaction.

Southern blot analysis of the genomic DNA of these 11 clones was performed and 3 clones were shown to have less than 3 intact copies of the pPytknlslacZDBcl construct.

Histochemical analysis of these 3 clones was performed by X-Gal staining as described in Bonnerot et al., *Methods in Enzymology, Guide To Techniques In Mouse Development*, Academic Press, pp. 451-469 (1993). Two (2) of 3 clones showed expression of β-galactosidase in less than $1 \times 10^6$ cells. β-galactosidase in these cells is probably the result of intragenic recombination of the 4 bp direct repeat inserted into the BclI restriction site. Northern blot analysis of the mRNA expressed by the integrated pPytknlslacZDBcl construct showed very little expression for one of the clones (the one with no background expression) and strong signals for two other clones (the ones expressing β-galactosidase in less than $1 \times 10^6$ cells). These two cell lines, NIH 3T3 DBcl1 and NIH 3T3 DBcl2, were selected to be the targets to the D-loop recombination.

Ex Vivo Recombination in NIH 3T3 DBcl1 and NIH 3T3 DBcl2 Cell Lines

Three sets of experiments were performed, in triplicate, using the NIH 3T3 DBcl1 and NIH 3T3 DBcl2 cell lines. Each set of experiment, in triplicate, comprises 8 different cotransfections of DNA mixes as shown in Table 1. Transfections were performed in either $5 \times 10^4$ NIH 3T3 DBcl1 cells or $5 \times 10^4$ NIH 3T3 DBcl2 cells in a 60 mm petri dish (Falcon) using the CaPO$_4$ precipitation method.

TABLE 1

| Mix Number | Expression Plasmid | Quantity | Repair Matrix | Quantity |
|---|---|---|---|---|
| 1 | pCMV I-SceI(+) | 9 µg | p2Wlac | 1 µg |
| 2 | pCMV I-SceI(+) | 9 µg | pWlac | 1 µg |
| 3 | pCMV I-SceI(+) | 9 µg | p-lac | 1 µg |
| 4 | pCMV I-SceI(+) | 9 µg | lac | 1 µg |
| 5 | pCMV I-SceI(−) | 9 µg | p2Wlac | 1 µg |
| 6 | pCMV I-SceI(−) | 9 µg | pWlac | 1 µg |
| 7 | pCMV I-SceI(−) | 9 µg | p-lac | 1 µg |
| 8 | pCMV I-SceI(−) | 9 µg | lac | 1 µg |

Ninety-six hours after transfection, cells were stained for β-galactosidase expression in X-Gal and blue colony forming units (bcfu) were counted. The number of bcfu is the result of the D-loop correction in each of the experiment. Results are shown in FIG. 2.

Transfection of NIH 3T3 DBcl2 cells with mix number 1 (pCMV I-SceI(+), 9 µg; p2Wlac, 1 µg) gave a 3 to 5% of β-galactosidase positive clones (out of three experiments) as the higher rate of D-loop correction of the pPytknlslacZDBcl mutated plasmid. Thus, after transfection of $1 \times 10^5$ cells with mix number 1, 96 individual cells were cloned by limit dilution according to standard methods. Cells were grown in DMEM, 10% calf serum, and analyzed for β-galactosidase expression. Five (5) of 71 clones showed more than $1 \times 10^6$ cells expressing β-galactosidase (ranging between 5 to 80% of the cells). Southern blot analysis of these 5 clones showed that 100% of the cells had their nlslacZ gene with a BclI site recovered. The lack of correspondence between the expression of the intact nlslacZ open reading frame and the total repair of the genome is probably the result of transgene variegation.

Example 3

Cell Line Production and D-Loop Recombination: Correction Of A 4 Base Pair Deletion 5 µg of the pPytknlslacZΔBcl plasmid and 5 µg of the pUSVneo plasmid were cotransfected in $5 \times 10^4$ NIH 3T3 cells (American Type Culture Collection) in a 35 mm petri dish (Falcon) using the CaPO$_4$ precipitation method. 48 hours after transfection, the tissue culture medium was supplemented with 600 µg/ml of Geneticin (Gibco BRL). Antibiotic selection was maintained during selection of Geneticin resistant clones and during subcloning. Forty-eight (48) Geneticin resistant clones were isolated and grown independently in Dulbeccos modified Eagles Medium (DMEM), 10% calf serum, for 15 days before evaluating for the presence of the nlslacZ gene.

To evaluate for presence of the nlslacZ gene, DNA was extracted from cells in all 48 cultures of Geneticin resistant clones. Fragments of the nlslacZ gene were amplified by PCR as described in *BioFeedback in BioTechniques*, Hanley & J. P. Merlie, Vol. 10, No. 1, p. 56T (1991). Forty-eight (48) of 48 clones were positive for the presence of the nlslacZ gene.

Twenty-four (24) of the 48 clones positive for the presence of the nlslacZ gene were evaluated for expression of the mutated nlslacZ gene. To evaluate for expression of the mutated nlslacZ gene, RNA was extracted from cells in the corresponding 24 cultures of Geneticin resistant clones. RNA encoding the mutated nlslacZ gene was amplified by RT-PCR. The oligonucleotide primer 5'-TACACGCGTCGTGATTAGCGCCG-3' (SEQ ID NO:5) was used for lacZ reverse transcription. PCR was performed as described in *BioFeedback in BioTechniques*, Hanley & J. P. Merlie, Vol. 10, No. 1, p. 56T (1991). Nine (9) of 24 clones showed a positive reaction.

Southern blot analysis of the genomic DNA of these 9 clones was performed and 1 clone was shown to have less than 3 intact copies of the pPytkulslacZΔBcl construct.

Histochemical analysis of these 4 clones was performed by X-Gal staining as described in Bonnerot et al., *Methods in Enzymology, Guide To Techniques In Mouse Development*, Academic Press, pp. 451-469 (1993). No clones showed expression of β-galactosidase. No intragenic recombination can occur in these cell lines. Northern blot analysis of the mRNA expressed by the integrated pPytknlslacZΔBcl construct showed very little expression for two of the clones and strong signals for the other two clones. These two cell lines, NIH 3T3 ΔBcl1 and NIH 3T3 ΔBcl2, were selected to be the targets to the D-loop recombination.

Ex Vivo Recombination in NIH 3T3 ΔBcl1 and NIH 3T3 ΔBcl2 Cell Lines

Three sets of experiments were performed, in triplicate, using the NIH 3T3 ΔBcl1 and NIH 3T3 ΔBcl2 cell lines. Each set of experiment, in triplicate, comprises 8 different cotransfections of DNA mixes as shown in Table 2. Transfections were performed in either $5 \times 10^4$ NIH 3T3 ΔBcl1 cells or $5 \times 10^4$ NIH 3T3 ΔBcl2 cells in a 60 mm petri dish (Falcon) by the $CaPO_4$ precipitation method.

TABLE 2

| Mix Number | Expression Plasmid | Quantity | Repair Matrix | Quantity |
| --- | --- | --- | --- | --- |
| 1 | pCMV I-SceI(+) | 9 μg | p2Wlac | 1 μg |
| 2 | pCMV I-SceI(+) | 9 μg | pWlac | 1 μg |
| 3 | pCMV I-SceI(+) | 9 μg | p-lac | 1 μg |
| 4 | pCMV I-SceI(+) | 9 μg | lac | 1 μg |
| 5 | pCMV I-SceI(−) | 9 μg | p2Wlac | 1 μg |
| 6 | pCMV I-SceI(−) | 9 μg | pWlac | 1 μg |
| 7 | pCMV I-SceI(−) | 9 μg | p-lac | 1 μg |
| 8 | pCMV I-SceI(−) | 9 μg | lac | 1 μg |

Ninety-six hours after transfection, cells were stained for β-galactosidase expression in X-Gal and blue colony forming units (bcfu) were counted. The number of bcfu is the result of the D-loop correction in each of the experiment. Results are shown in FIG. 2.

Transfection of NIH 3T3 ΔBcl2 with mix number 1 (pCMV I-SceI(+), 9 μg; p2Wlac, 1 μg) gave a 1 to 3% of β-galactosidase positive clones (out of the three experiments) as the higher rate of D-loop correction of the pPytknlslacZΔ-Bcl mutated plasmid. Thus, after transfection of $1 \times 10^5$ cells with mix number 1, 96 individual cells were cloned by limit dilution. Cells were grown in DMEM, 10% calf serum, and analyzed for β-galactosidase expression. Two (2) of 66 clones showed cells expressing β-galactosidase (ranging between 30 to 80% of the cells). Southern blot analysis of these 2 clones showed that 100% of the cells had their nlslacZ gene with a Bcl I site recovered. The lack of correspondence between the expression of the intact nlslacZ open reading frame and the total repair of the genome is probably the result of transgene variegation.

Example 4

I-SceI Induced D-loop Recombination

The pPytknlslacZD-Bcl construct is integrated into the genomic DNA of NIH 3T3 cells as described in Example 2. In these cells, the nlslacZDBcl gene is transcribed but β-galactosidase expression is not detected (β-gal⁻ cells). β-gal⁻ cells are cotransfected with the p2Wlac plasmid containing two I-SceI sites and an expression vector coding for I-SceI endonuclease. The p2Wlac plasmid is linearized in vivo by the I-SceI endonuclease and corrects the DBcl mutation by D-loop recombination. As a result, these cells contain a pPytknlslacZ plasmid that expresses β-galactosidase (β-gal⁺ cells). A schematic diagram of this experiment is depicted in FIG. 1.

The teachings of all the articles, patents and patent applications cited herein are incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of attenuating expression of an endogenous gene of interest in a cell in vitro, said method comprising:
   a) introducing into the cell a vector comprising targeting DNA, wherein said targeting DNA is flanked by a restriction endonuclease site and comprises (1) DNA homologous to a targeting site of the endogenous gene of interest and (2) DNA which attenuates expression of the gene of interest by recombination between said targeting DNA and the gene of interest; and
   b) introducing into the cell a restriction endonuclease which cleaves the restriction endonuclease site, thereby increasing the probability of recombination between said targeting DNA and the gene of interest, and thereby increasing the probability of obtaining a cell with the expression of the endogenous gene of interest being attenuated.

2. The method of claim 1 wherein the vector is a viral vector.

3. The method of claim 1 wherein said targeting DNA is flanked by two restriction endonuclease sites.

4. A method of introducing a mutation into a target site of chromosomal DNA of a cell in vitro, said method comprising:
   a) introducing into the cell a vector comprising targeting DNA, wherein said targeting DNA is flanked by a restriction endonuclease site and comprises (1) DNA homologous to the target site and (2) the mutation to be introduced into the chromosomal DNA; and
   b) introducing into the cell a restriction endonuclease which cleaves the restriction endonuclease site, thereby increasing the probability of recombination between said targeting DNA and the target site of the chromosomal DNA, and thereby increasing the probability of obtaining a cell with the mutation introduced into the target site of the chromosomal DNA.

5. The method of claim 4 wherein the vector is a viral vector.

6. The method of claim 4 wherein said targeting DNA is flanked by two restriction endonuclease sites.

7. A method of modifying a specific sequence in chromosomal DNA of a cell in vitro, said method comprising:
   a) introducing into the cell a vector comprising targeting DNA, wherein said targeting DNA is flanked by a restriction endonuclease site and comprises (1) DNA comprising a sequence homologous to the specific sequence to be modified and (2) DNA which results in modification of the specific sequence by recombination between said targeting DNA and the chromosomal DNA; and
   b) introducing into the cell a restriction endonuclease which cleaves the restriction endonuclease site, under conditions appropriate for the restriction endonuclease to cleave the restriction endonuclease site, thereby increasing the probability of recombination between said targeting DNA and the chromosomal DNA, and thereby increasing the probability of obtaining a cell with the specific sequence modified in the chromosomal DNA.

8. The method of claim 7 wherein the vector is a viral vector.

9. The method of claim 7 wherein said targeting DNA is flanked by two restriction endonuclease sites.

* * * * *

SEQUENCE LISTING

<160> NUMBER OF SEQ ID NOS: 5

<210> SEQ ID NO 1
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 1
ctagatgcat agggataaca gggtaat                                    27

<210> SEQ ID NO 2
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 2
agctattacc ctgttatccc tatgcat                                    27

<210> SEQ ID NO 3
<211> LENGTH: 27
<212> TYPE: DNA
<213> ORGANISM: Artificial Sequence
<220> FEATURE:
<223> OTHER INFORMATION: Synthetic Oligonucleotide

```
<400> SEQUENCE: 3
gatcatgcat agggataaca gggtaat                                    27

<210> SEQ ID NO 4
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 4
ctagattacc ctgttatccc tatgcat                                    27

<210> SEQ ID NO 5
<211> LENGTH: 23
<212> TYPE: DNA
<213> ORGANISM: Artificial Sequence
<220> FEATURE:
<223> OTHER INFORMATION: Synthetic Oligonucleotide Primer

<400> SEQUENCE: 5
tacacgcgtc gtgattagcg ccg                                        23
```